United States Patent [19]

Lohr

[11] Patent Number: 4,730,933
[45] Date of Patent: Mar. 15, 1988

[54] PHOTOMETRIC MEASURING APPARATUS

[76] Inventor: Willi Lohr, Ginsterweg 75, D-7547 Wildbad, Fed. Rep. of Germany

[21] Appl. No.: 930,472

[22] Filed: Nov. 14, 1986

[30] Foreign Application Priority Data

Nov. 16, 1985 [DE] Fed. Rep. of Germany ....... 3540823

[51] Int. Cl.[4] .................... G01N 21/13; G01N 21/01
[52] U.S. Cl. .................................. 356/440; 356/244; 356/434; 356/436
[58] Field of Search ............... 356/434, 436, 440, 244

[56] References Cited

U.S. PATENT DOCUMENTS

| 3,951,609 | 4/1976 | Palenscar | 356/244 X |
| 4,319,842 | 3/1982 | Priarone et al. | 356/244 X |
| 4,586,818 | 5/1986 | Lohr | 356/244 |
| 4,674,876 | 6/1987 | Rossiter | 356/244 |

Primary Examiner—Eugene R. LaRoche
Assistant Examiner—Nathan McCutcheon
Attorney, Agent, or Firm—Armstrong, Nikaido, Marmelstein & Kubovcik

[57] ABSTRACT

A photometric measuring apparatus having a measuring chamber which can be cut off from extraneous light when a sample vessel is inserted and removed from the open end of the measurement chamber. A plunger, having a light-tight seal, movable vertically and horizontally on a pivotable arm driven by a drive mechanism for sealing the measuring chamber after a sample vessel is inserted in the measuring chamber. A guide means comprising a cylindrical guide tube having a guide groove on its surface which acts as cam means for controlling the vertical and horizontal movement of the plunger. The drive mechanism includes a drive motor and photocells for controlling the drive of the motor and vertical movement of the plunger and drive of the motor until the sample vessel upon which measurements have been completed are removed. The drive motor is spring mounted and actuates a microswitch to interrupt the motor drive when the drive is obstructed by the operator.

11 Claims, 7 Drawing Figures

PHOTOMETRIC MEASURING APPARATUS

This invention relates to a photometric measuring apparatus, more particularly, to such an apparatus with a measuring chamber which can be isolated from extraneous light, and in which a test tube, or the like, can be sealed in the chamber from light by means of a plunger having a light-tight mechanism, the plunger being held on a vertically slidable and horizontally pivotable arm.

In presently commercialized measuring apparatus, such as being presenting sold commercially by the assigned hereof, the vertically slidable and horizontally pivotable arm for vertical and horizontal movement, is held in a cylindrical guide which extends parallel to the measuring chamber. The movement is as follows: In the rest state, the arm rests with its longitudinal axis on the imaginary line joining the cylindrical guide and the measuring chamber, and above the measuring chamber with the plunger in the measuring chamber. When it is desired to insert a test tube, the arm is first lifted vertically until the plunger is free of the measuring chamber. Then, by pressing a control button the arm can be swung in a 90° arc, so that the opening of the measuring chamber is accessible for inserting a test tube. After the test tube is inserted, the arm is then swung back to its initial position, where the longitudinal axis of the plunger is coaxial with that to the measuring chamber. Then the arm is lowered, so that the end face of the plunger presses against the upper edge of the test tube and moves the test tube into the prescribed measuring position. At the same time, the plunger optically seals the measuring chamber.

The foregoing arm movement is carried out manually. It is time consuming. This is a particularly significant, when measurements are to be performed on multiple series of samples, because the apparatus is not operating during the manual manipulation period. This "dead time" is high compared to the actual measuring time.

An object of the present invention is to improve a measuring station of the type described by speeding up the movement. At the same time, the operation is made safer.

This object is achieved in the present invention by a drive mechanism which controls the vertical and horizontal movement of the arm and plunger.

The drive mechanism enables complete automation of the insertion and removal of the sample while insuring error-free operation of the measuring apparatus.

In a refinement of the invention, the guide means comprises a cylindrical guide tube running parallel to the measuring chamber and having a guide groove in its surface which guide groove acts as a cam means. The drive mechanism drives a shaft which moves the guide tube and produces vertical and angular positions of the guide tube according to the configuration of the guide groove.

The rotary movement delivered by the drive mechanism is converted into vertical movement of the cylindrical guide tube by the shaft. According to a further refinement, the guide tube is guided in a bearing block which is rigidly connected to the housing block. A cam follower means is disposed in the guide bore of the bearing block. The cam follower means engages the guide groove of the guide tube.

By joining the bearing block to the measuring chamber housing block to fix the position of the bearing block, and by configuring the guide groove the arm and plunger can be swung horizontally when the guide tube is moved vertically, in addition to moving the arm and plunger vertically along with the guide tube. Such horizontal movement is due to the horizontal component in the course of the guide groove in the guide tube. Thus, the plunger moves in a path which is an image of the guide groove. Accordingly, the configuration of the guide groove can be adapted to define the optimal course of movement of the plunger inside and outside the measuring chamber, between the two end positions of the plunger.

In a further improvement, the drive mechanism is held against a secondary support element wherewith the drive mechanism is upwardly and downwardly slidable. A microswitch is mounted on the secondary support element. Sliding of the drive mechanism is carried out against the force of a spring acting between two elements, namely the support plate, which ultimately supports the drive mechanism, and the secondary support element. This provides operational safety of the automatically controlled measuring station of the invention. When an obstacle, such as the operator's finger, is present in the movement path of the arm or plunger, there is a limit to the force the plunger will apply to the obstacle. After a short period of time, unless the obstacle is removed, the microswitch will shut off the drive mechanism. This is achieved by the drive mechanism which is pulled up by the shaft which continues to rotate. The drive mechanism is thereby moved against the associated contact of the microswitch. During ordinary, proper functioning, the vertical component of the movement of the plunger results in relative movement between the plunger and the drive mechanism. When the plunger or arm becomes blocked such relative vertical movement is converted to a vertical upward movement of the drive mechanism until the latter reaches the point where it is shut off.

In another feature of the invention, a photocell system is provided above the bottom of the test tube when the test tube in the measuring position. The photocell system controls the drive mechanism, inactivating the drive until the bottom of the test tube, which has undergone measurement, has passed the photocell system when the test tube is removed. This embodiment improves safety and prevents improper operation.

The photocell system prevents double measurements, which can occur with manual operation of a device of the type described. After a measurement is carried out and the arm, with associated plunger, is returned to its upper, swung-away position, the drive mechanism can only be activated and the plunger swung back toward the measuring chamber if the test tube, which has already undergone measurement, re-passes the photocell. This can only occur if the test tube has been withdrawn from the measuring chamber, as intended.

In still another feature, the underside of the plunger has a seal which has a protective ring on its underside. The plunger is guided in the measuring chamber in a bushing, such as tetrafluroethylene material with a carbon filler material therein.

The protective ring is of metallic material and allows the plunger to engage the test tube in the measuring chamber without wear and tear. The bushing is inserted in the upper part of the chamber as a guide for the plunger. The bushing material reduces the sliding wear of the advanced seal which optically seals the chamber. Because of the protective ring, the underside of the advanced seal does not come into direct contact with the upper edge of the test tube. The overall load on the advanced seal and persistent mechanical deformations are reduced. Damage to the optical seal is reduced and a longer service life of the rubber material used for the advanced seal is attained.

One feature which enables the metal protective ring to be employed is the automatic guiding of the plunger by the guide cam means in the guide cylinder. This provides accurate centering of the plunger coaxially with the test tube and coaxially with the measuring chamber.

The tetrafluroethylene bushing with a corresponding accurately cut interior bore for the plunger also allows a somewhat greater tolerance for the bore for the bushing in the housing block.

Additional photocell arrangements are provided to define the two end positions of the guide means, the arm and plunger. Such photocell arrangements control the drive mechanism. Thus, the operation of the measuring stations is reduced to actuating the control switch of the drive mechanism twice—once after inserting the test tube into the measuring chamber and once after the measurement has been completed.

An exemplary embodiment of the inventive measuring station will now be described in more detail, with references to the drawings.

Figure 1:
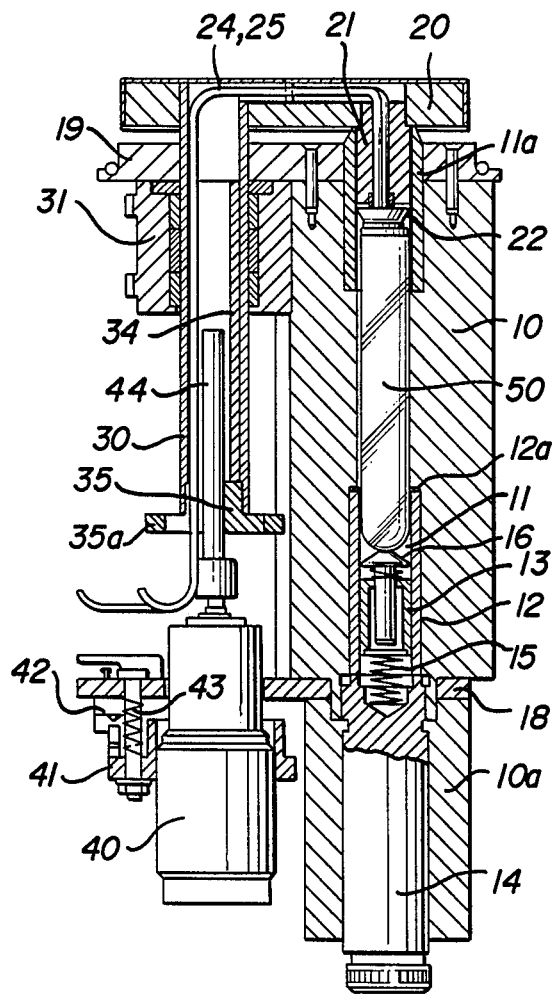
FIG. 1 shows a longitudinal cross section through the measuring apparatus of the instant invention with the plunger in the measuring chamber.

Referring to the drawings, the measuring apparatus of the instant invention includes housing block 10, in which the measuring station 11 is disposed; bearing block 31 connected to housing block 10 in fixed position and in which guide tube 30 is disposed; support plate 18 attached to the lower end of housing block 10; drive mechanism 40 disposed coaxially with guide tube 30 and supported in housing block 10; and, an arm 20 attached to the upper end of the guide tube 30. Plunger 21 is mounted adjacent the free end of arm 20. The upper end faces of the housing block 10 and the bearing block 31 are flush with each other and are connected by a common cover plate 19 bolted to the housing block 10.

Measuring chamber 11 is surrounded by a bushing 11a of tetrafluroethylene material with carbon filler material. Bushing 11a passes through cover plate 19 and into the upper region of housing block 10. Measuring chamber interior tube 12 is disposed in the lower region of housing block 10. Tube 12 has, in its interior, sealing sleeve 13 in which support rod or plunger 16 is mounted for vertical slidable movement. The tip or upper end of rod 16 is conical. The apex of the cone tip of rod 16 has a concave cavity for receiving the bottom of test tube 50 for centering the longitudinal axis of test tube 50 with the longitudinal axis of measuring chamber 11. Sealing sleeve 13, in tube 2, is supported from below by spring 15, which engages a socket on the upper end face of a plug fitting 14, screwed into the lower portion 10a of housing block 10. The upper end of the measuring chamber interior tube 12 is sealed by sealing ring 12a.

Figure 2:
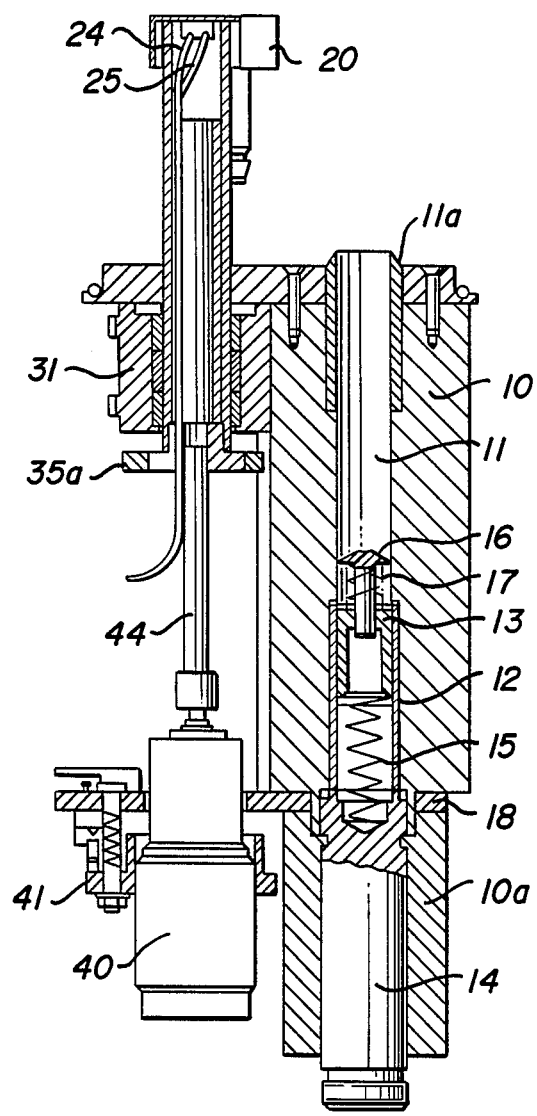
FIG. 2 is a longitudinal cross section similar to FIG. 1 with the plunger pulled out of and swung away from the measuring chamber.

Support rod 16 is also supported by spring 17, engaged, at one end, against the end face of the sealing sleeve 13, so that, when there is no test tube in measuring chamber 11, the support rod 16 assumes it upper position relative to the sealing sleeve 13. The spring forces of spring 17 are selected so that, in the position shown in FIG. 2, the test tube is pushed out of measuring chamber 11, after completion of the measurement, with the upper end of the test tube extends above bushing 11a so that the test tube end can be grasped by the operator. The upper position of support rod 16 is determined by a shoulder on the end of the cylindrical shaft of the support rod 16. In the upper position, the shoulder of support rod 16 rests against an inner ring-shaped shoulder of sealing sleeve 13 and prevents light from reaching the photomultiplier whenever there is no test tube in the measuring chamber 11.

Guide tube 30 is vertically slidable in bearing block 31 and is sealed off, at its lower end, by bushing 35 having a connecting collar 35a. An interior tube 34 is held coaxially in guide tube 30 and accommodates flexible injection tubes 24, 25 which extend into arm 20 and plunger 21. Bushing 35 engages shaft 44 attached coaxially to the drive shaft of a motor 40 and extends into the interior space of tube 34. Drive motor 40 is connected to support plate 18 via three cylindrical guides, only one being shown in FIG. 1. Secondary support element 41, which bears the motor 40, is vertically slidable upward against the force of spring 43. The switch contact of microswitch 42, disposed on the underside of the support plate 18, is attached on the secondary support element 41 and is actuated upon vertical upward motion of secondary support element 41 with motor 40. Motor 40 is controlled by photocells 45, 46, FIG. 3, which are actuated by fitting 35a on bushing 35. The distance between photocell 45, 46 determines the length of movement of guide tube 30 under the action of shaft 44.

Figures 4, 5:
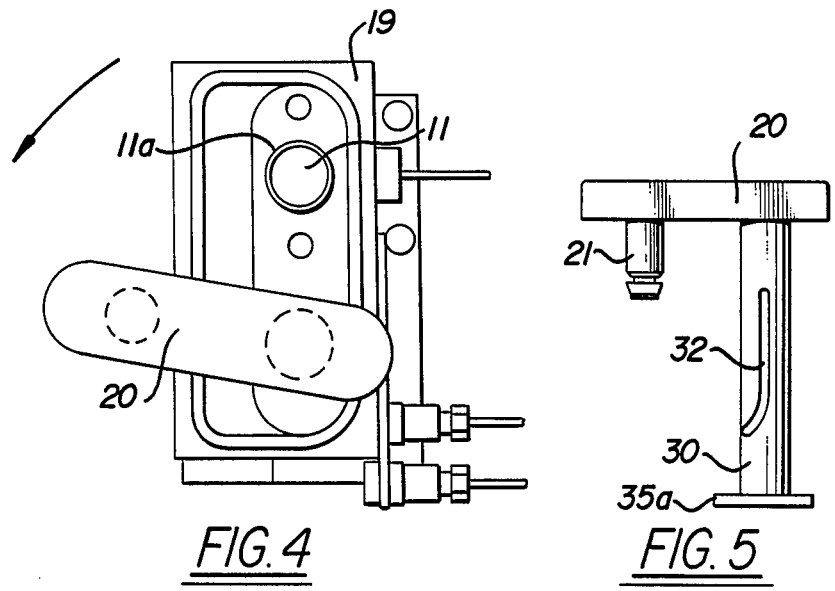
FIG. 4 is a top plan view of the measuring apparatus with the arm swung away.
FIG. 5 is a side view of the plunger connected to the guide tube via the arm.
Figures 6, 7:
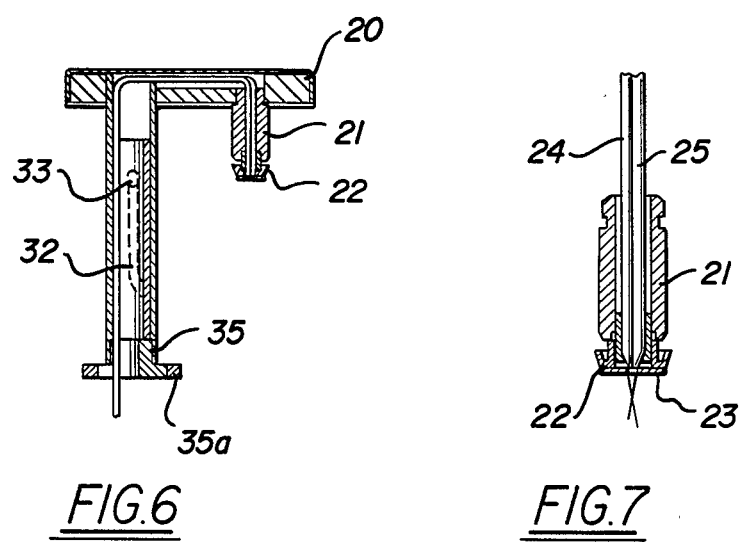
FIG. 6 is a longitudinal section view of the apparatus of FIG. 5 taken from the back of FIG. 5.
FIG. 7 is cross sectional enlarged view of the plunger of FIG. 6.

Guide groove 32 FIG. 5, in the surface of guide tube 30, engages guide cam follower 33 of bearing block 31 FIG. 1. The upper part of guide groove 32 extends vertically for a length which is at least equal to the unobstructed height of the plunger 21. The movement of shaft 44 is converted exclusively into vertical movement of guide tube 30 as long as the plunger 21 is disposed inside tetrafluroethylene bushing 11a of the measuring chamber 11. The lower portion of the guide groove 32, FIG. 5, has a curved configuration causing guide tube 30 to rotate in the bearing block 31, in addition to vertical translational motion therein, when guide cam follower 33 reaches the lower portion of guide groove 32. Accordingly, plunger 21 (FIGS. 5 and 6), rigidly connected to guide tube 30 by arm 20, moves both vertical and horizontal. After leaving measuring chamber 11, plunger 21 is lifted farther vertically and is swung laterally, thereby exposing the opening of the measuring chamber 11.

Ring-shaped seal 22 is mounted on the lower end of plunger 21. Seal 22 has a metallic protective ring on its lower end, which ring presses against test tube 50. Two flexible injecting tubes 24, 25 are passed through the plunger 21 and extend through arm 20 and interior tube 34.

Figure 3:
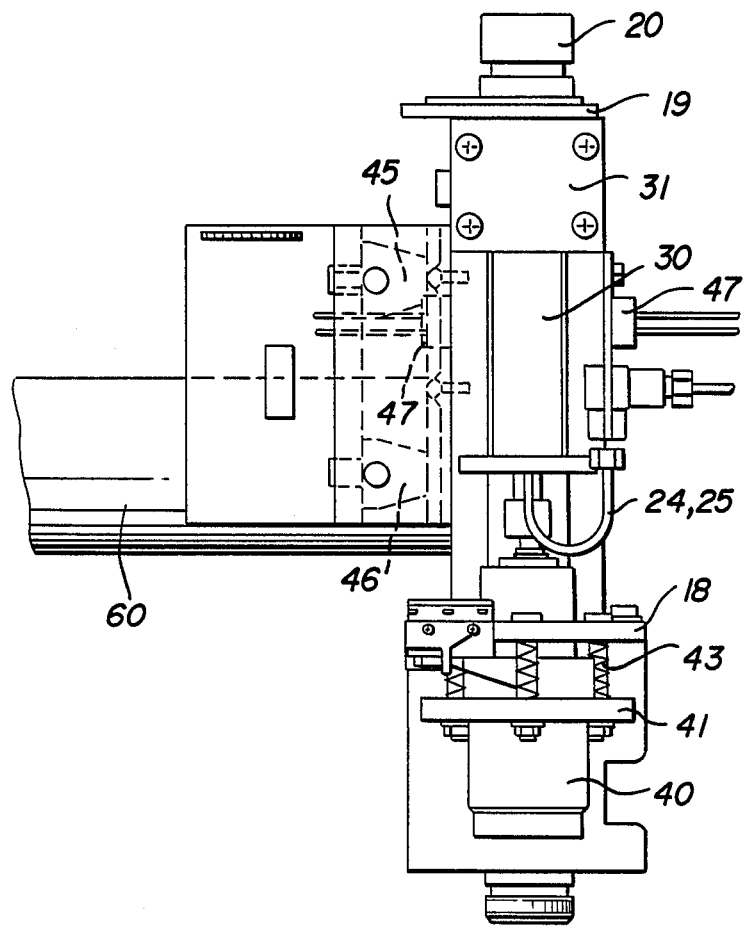
FIG. 3 is a side view of the measuring apparatus of FIG. 1, taken from the left of FIG. 1 and in the direction toward the drive mechanism.

The lower region of housing block 10 has, in known fashion, a cylindrical recess (not shown) for mounting photomultiplier 60, FIG. 3.

Motor control photocell system 47 is provided above the bottom of test tube 50 in the measuring position of the test tube (FIG. 1), and controls motor 40 so plunger 21 can only be lowered into the measuring chamber 11 when the test tube 50 upon which measurements have been completed has been removed from the measuring chamber, that is, the bottom of the test tube upon which measurements are completed past, upwardly, photocell system 47.

The operation of the above-described measuring station is as follows:

In the starting position (FIG. 2), the guide tube 30 is in its upper end position and plunger 21 is in the swung-out position, so that the upper opening of measuring chamber 11 is accessible. Test tube 50 upon which measurements are to be made is then inserted into the measuring chamber, in known fashion, until the test tube engages and is held in the dish-shaped upper end face of the support rod 16, which centers the test tube. Motor 40 is then started, via a switch, not shown, and shaft 44 pulls the guide tube downward. As a result of the curved configuration of guide groove 32, plunger 21 is swung into a position coaxial with the axis of the measuring chamber and moves downward. Protective ring 23 becomes disposed coaxially with the test tube 50. As the guide tube 30 moves farther downward in the straight portion of guide groove 32, plunger 21 is guided into the tetrafluroethylene bushing 11a and plunger 21 presses test tube 50 downward against ejection spring 17, compressing the spring. Plunger 21 presses sealing sleeve 13 downward against the action of spring 15, exposing the measuring opening of the photomultiplier 60. The upper end of the measuring chamber 11 is sealed off against light by advanced seal 22. In the measuring position, FIG. 1, the lower photocell system 46 shuts off the motor 40, whereby, in known fashion, the measurement of the sample in test tube 50 can begin with appropriate reagents, where required, injected via the flexible injection tubes 24, 25.

After the measurement is concluded, motor 40 is restarted by actuation of the appropriate switch. Shaft 44 is rotated in the direction opposite to its initial direction of rotation, causing the guide tube 30 to slide back upward, whereby the plunger 21 is raised out of the tetrafluroethylene bushing 11a. At the same time, the sealing sleeve 13 closes off the measuring opening of the photomultiplier 60, under action of spring 15, prior to the time that the advanced seal 22 of plunger 21 re-exposes the opening of the measuring chamber 11. Finally, cam follower 33 in bearing block 31 reaches the curved part of guide groove 32, so that, in the final segment of its excursion, plunger 21 is moved farther upward and simultaneously is swung laterally. After the test tube 50 is released by the protective ring 23, the released test tube is pushed upward by support rod 16 under the action of the ejection spring 17, until the upper edge of the test tube extends above bushing 11a. The test tube can then be readily removed. The motor 40 is again shut off via the upper photocell system 45. This completes one measuring cycle.

The next measuring cycle may only begin when the photocell system 47 releases the motor 40, i.e. when the bottom of measured test tube has been moved upwardly and has reached a position above the ejecting rod 16. This safety switching system ensures that each test tube upon which measurements are completed will be removed from the measuring chamber and will not be measured a second time. Particularly during a series of measurements, matching and identification problems can occur as a result of unintended repeated measurements, and, when the measuring station is used in a medical context, can have grave consequences for the patients concerned.

If some impediment should arise in the movement path of the arm or the plunger, preventing further lowering of the plunger, e.g. as a result of an object or a finger being interposed, then as a result of the relative movement of the motor 40 and the arm 20 produced by the rotation of the shaft 44, the motor 40 will be pulled toward the support plate 18 against the force of the springs 43, until the point is reached that the microswitch 42 is actuated and the motor 40 is shut off. This also ensures that only test tubes of regulation size are used. The "floating" suspension of the motor 40 on the support plate 18, and the additional control of the motor by means of the photocell system 47, are important safety features of the inventive measuring station which provides a safe, fully automatic course of measurement.

What is claimed:

1. A photometric measuring apparatus having a measuring chamber with an open top for receiving a sample vessel containing material to be measured, a first sealing means in said chamber for sealing said measuring chamber from extraneous light when said sample vessel is removed, a plunger for insertion into said open top of said measuring chamber after a sample vessel to be measured is positioned in said measuring chamber, a second sealing means on said plunger for sealing said measuring chamber from extraneous light when said plunger is inserted into said open top of said measuring chamber, a vertically slidable and horizontally pivoted arm on said plunger for pivoting said plunger and aligning said plunger with said open top of said measuring chamber characterized in a guide means for guiding said vertically slidable and horizontally pivotal arm for vertical and pivotal movement and a drive mechanism for driving and controlling said vertical and horizontal movement of said arm and said plunger.

2. A photometric measuring apparatus, as recited in claim 1 further characterized in that said guide means comprises a cylindrical guide tube running parallel to said measuring chamber, said guide tube having a guide groove acting as a cam means, said drive mechanism including a drive shaft for driving said guide tube vertically and angularly in conformance with said guide groove of said guide tube.

3. A photometric measuring apparatus as recited in claim 2, further characterized in that said guide tube has a flexible interior tube for receiving flexible injection tubes.

4. A photometric measuring apparatus as recited in claim 2, further characterized by a housing block, a bearing block rigidly connected to said housing block, said bearing block guiding said guide tube and having a guide bore and cam follower means disposed in said guide bore of said bearing block, said cam follower means engaging said guide groove of said guide tube.

5. A photometric measuring apparatus as recited in claim 2 further characterized in that said guide means further comprises a bushing, said guide tube being mounted on said bushing, said bushing having an interior engaging said drive shaft, said drive shaft extending from said bushing into the interior of said guide tube and interior tube.

6. A photometric measuring apparatus as recited in claim 1 further characterized in that said guide means has two end positions and a pair of photocells for controlling said drive mechanism for driving said guide means between said two positions.

7. A photometric measuring apparatus as recited in claim 1 further characterized in that said drive mechanism includes a secondary support element and a microswitch mounted on said secondary support element, said drive mechanism being slidable vertically upward in said secondary support element.

8. A photometric measuring apparatus as recited in claim 7, further characterized in that said drive mechanism further includes a support plate and a spring between said support plate and said secondary support element, said driving mechanism acting against the force of said spring.

9. A photometric measuring apparatus as recited in claim 1 further characterized in that said plunger has an advanced seal having a protective ring on its underside.

10. A photometric measuring apparatus as recited in claim 1 further characterized in that said measuring chamber has a carbon filled tetrafluroethylene bushing for guiding said plunger.

11. A photometric measuring apparatus as recited in claim 1 further characterized in that said measuring chamber includes a photocell system mounted in said measuring chamber above the bottom of a test tube when said test tube is in measuring position in said chamber, said measuring chamber photocell system controlling said drive mechanism for inactivating said drive mechanism until the bottom of a test tube which has completed measurement has been raised in said measuring chamber to a position above said measuring chamber photocell system.

* * * * *